United States Patent [19]

Mellberg

[11] 4,165,366

[45] Aug. 21, 1979

[54] DENTAL PROPHYLACTIC PASTE

[75] Inventor: James R. Mellberg, Pottersville, N.J.

[73] Assignee: Colgate Palmolive Company, New York, N.Y.

[21] Appl. No.: 872,841

[22] Filed: Jan. 26, 1978

[51] Int. Cl.$^2$ ............................ A61K 7/16; A61K 7/22
[52] U.S. Cl. ...................................... 424/49; 424/54; 424/357
[58] Field of Search ................................ 424/49–58, 424/357

[56] References Cited

U.S. PATENT DOCUMENTS

| | | | |
|---|---|---|---|
| Re. 15,691 | 9/1923 | Pfanstiehl | 424/55 |
| 1,275,275 | 8/1918 | Levinson | 424/49 |
| 1,445,351 | 2/1923 | Pfanstiehl | 424/55 |
| 1,445,352 | 2/1923 | Pfanstiehl | 424/55 |
| 1,467,024 | 9/1923 | Bergve | 424/49 |
| 1,516,206 | 11/1924 | Pfanstiehl | 424/55 |
| 1,528,422 | 3/1925 | Helsley | 424/55 |
| 1,947,635 | 2/1934 | Bergve | 424/49 |
| 2,089,531 | 8/1937 | Bergve | 424/55 |
| 2,470,906 | 5/1949 | Taylor | 424/55 |
| 3,228,845 | 1/1966 | Najjar | 424/49 |
| 3,257,282 | 6/1966 | Muhler | 424/52 |
| 3,337,412 | 8/1967 | Elbreder | 424/151 |
| 3,892,843 | 7/1975 | Muhler et al. | 424/52 |

*Primary Examiner*—Shep K. Rose
*Attorney, Agent, or Firm*—Robert L. Stone; Murray M. Grill; Herbert S. Sylvester

[57] ABSTRACT

A high viscosity, low spatter dental prophylactic paste including an abrasive, a humectant, a soluble alkaline silicate and an acid-forming agent, the ratio of the acid-forming agent to silicate being such as to delay the gelling time of the paste so that it is sufficiently flowable to be poured into individual containers via nozzles under low pressure before gelling.

11 Claims, No Drawings

DENTAL PROPHYLACTIC PASTE

This invention relates to prophylactic pastes used in dentistry for the periodic cleaning of teeth.

Many dentists prefer to use prophylactic pastes in the form of silicate gels. Solutions of a soluble alkaline silicate in a humectant gel almost instantaneously when neutralized with acid. When an abrasive is then added to form the paste, the flowability of the paste is decreased to the point where it is very difficult to pour the paste through nozzles under relatively low pressure into containers. Moreover, the gelled paste so formed has a poor appearance and is frequently crumbly and contains air pockets.

It is the primary object of this invention to provide a prophylactic dental paste containing an acid-forming agent and a soluble alkaline silicate wherein the gelling time thereof is increased sufficiently so that the gelling takes place at the final stage, namely, in the container into which it is poured via nozzles under relatively low pressure.

Another object of the invention is to provide a prophylactic dental paste of the character described in which the appearance of the paste is enhanced because the mixing of the abrasive into the solution of a soluble alkaline silicate, acid-forming agent and humectant can be more easily accomplished prior to gelling, thereby resulting in a more even distribution of the abrasive and an absence of air bubbles or pockets.

Another object of the invention is to provide a prophylactic dental paste of the character described having a gelling time up to and in excess of 24 hours at room temperature, but which can be gelled within about 30–60 minutes when heated to about 60° C., if so desired.

Yet another object of the invention is to provide a prophylactic dental paste with increased gelling time and enhanced appearance which does not thin out when used with a conventional rubber cleaning cup and possesses low spatterability.

The foregoing objects are obtained by providing a solution of a soluble alkaline silicate, preferably sodium metasilicate, and an acid-forming agent, preferably succinic anhydride, in a humectant, preferably glycerol and adding to this solution or liquid phase an abrasive, preferably pumice, the ratio of the anhydride to the silicate being such as to delay the gelling of the paste until such time as it is delivered through nozzles under relatively low pressure into containers where the paste ultimately gels.

The closest prior art known to applicant are the Najjar U.S. Pat. No. 3,228,845 and the Peeler U.S. Pat. No. 2,968,572. Najjar discloses a prophylactic dental paste which combines about 50% pumice flour, about 20–25% glycerine, about 12% water, up to about 2% agar-agar and up to about 10% sodium silicate which he states is non-splattering and flows evenly and smoothly under pressure without settling of the pumice flour for packaging the paste in capsules. A commercial product is marketed under said patent by Janar Company of Grand Rapids, Michigan as Nupro. Najjar claims that the agar-agar and sodium silicate coact synergistically to create flowability.

Peeler discloses applying to soil an aqueous mixture of an alkali metal silicate and an amide to solidify and stabilize the soil, the proportion of silicate to amide being such as to yield a gelling time of ½ to 8 hours at temperatures generally from 32° F. to about 180° F., so that the solution can be pumped and uniformly applied especially in subsoil injection.

The instant invention provides a high viscosity, low spatter, non-creamy prophylactic dental paste with delayed gelling action combining an abrasive, a humectant, a soluble alkaline silicate and an acid-forming agent.

The acid-forming agent may be an anhydride, such as succinic, acetic, maleic or fumaric anhydride, an amide such as formamide or acetamide, or an ester such as glyceryl diacetate or glyceryl triacetate, preferably succinic anhydride, in an amount of about 2–5% by weight of the final paste.

The soluble alkaline silicate may be an alkali metal silicate, such as sodium metasilicate or potassium metasilicate or quaternary ammonium silicate, preferably sodium metasilicate, in an amount of about 5–10% by weight of the final paste. The soluble silicates are composed of varied proportions of $Na_2O$, $SiO_2$ and $H_2O$. Philadelphia Quartz markets soluble silicates whose properties and application are described in its PQ Chemicals Bulletin 17-1. While sodium metasilicate nonahydrate is preferred, applicant has found that sodium silicate solutions PQ "Q" and PQ "N" set forth in said Bulletin can also be utilized effectively in the paste.

The preferred abrasive is medium grade pumice, although other abrasives may be used such as zirconium silicate, alumina, cerium oxide, silicon carbide and the like in an amount of about 40–60% by weight of the final paste.

The preferred humectant is glycerol although, here again, other humectants may be employed, such as propylene glycol and other non-toxic glycols. The humectant content in the final paste is about 15–45% by weight. In the liquid phase of the paste, i.e. the phase containing the humectant, the acid-forming agent and the soluble alkaline silicate, before the abrasive is added, the silicate is present in an amount of about 10–20% by weight and the acid-forming agent in an amount of about 5–9% by weight.

The final paste may be formulated to include neutral fluorides such as the alkali metal fluorides and, of course, appropriate flavoring, sweetening, coloring and preservative agents.

In preparing the paste, a solution of the silicate, humectant and acid-forming agent is made up. Since the use of an acid instead of an acid-forming or releasing agent causes an immediate gelling of the silicate, the ratio of the silicate to the acid-forming agent is such as to delay the gelling by about at least one hour and, as examples hereinafter show, the gelling is delayed at various ratios of silicate to acid-forming agent up to and beyond 24 hours. To the solution of the silicate and the acid-forming agent in the humectant the abrasive is added with mixing at room temperature for a time sufficient to obtain a substantially homogeneous paste. The mixing of the abrasive in the non-aqueous solution is readily effected because of the delayed gelling of the silicate, and while the mass is still ungelled, it is pumped under very low pressure through a nozzle into individual containers where the paste finally gels to form discs, capsules and the like. The gelled paste is substantially non-spattering and non-thinning when used by the dentist to apply to the teeth by means of a conventional rubber prophylaxis cup.

In the following Table are non-limitative examples of solutions of soluble alkaline silicates and acid-forming agents in humectants showing the delayed gelling action, it being understood that the final prophylactic dental paste will be made by adding to the solutions abrasive and, if desired, optional ingredients such as coloring, flavoring, sweetening and preservative agents.

pH of 9.0 and solutions of sodium metasilicate .9H$_2$O gelled slightly below a pH of 8.5.

The following are non-limitative examples of the final prophylactic dental pastes of the instant invention.

TABLE

| | Silicate | Humectant | Acid-Forming Agent | Gel Time Room Temperature | 60° C. |
|---|---|---|---|---|---|
| (1) | 2.5g Na metasilicate .9H$_2$O(SMS) | 10g Glycerol | 0.7ml acetic anhydride (AA) | >4 days | 2 hrs. |
| (2) | 2.5g Na metasilcate .9H$_2$O(SMS) | 10g Glycerol | 0.8ml AA | >4 days | 2 hrs |
| (3) | 2.5g Na metasilicate .9 H$_2$O(SMS) | 10g Glycerol | 0.9ml AA | >4 days | 2 hrs. |
| (4) | 2.5g Na metasilicate .9H$_2$O(SMS) | 10g Glycerol | 1.0ml AA | >4 days | 2 hrs. |
| (5) | 2.5g Na metasilicate .9H$_2$O(SMS) | 10g Glycerol | 0.9ml AA | Began to gel at 5 hrs. | |
| (6) | 2.5g Na metasilicate .9H$_2$O(SMS) | 10g Glycerol | 1.0ml AA | Began to gel at 3 hrs. | |
| (7) | 2.5 g Na metasilicate .9H$_2$O(SMS) | 10g Glycerol | 1.1ml AA | Began to gel at 2 hrs. | |
| (8) | 2.5g Na metasilicate .9H$_2$O(SMS) | 10g Gycerol | 1.2ml AA | Began to gel at 1 hr. | |
| (9) | 2.75g SMS | 5g Glycerol | 0.9g succinic anhydride (SA) in 7g glycerol | Gelled overnight | |
| (10) | 2.75g SMS | 5g Glycerol | 1.0g SA in 7g of glycerol | Gelled overnight | |
| (11) | 2.75g SMS | 5g Glycerol | 1.1g SA in 7g of glycerol | Gelled overnight | |
| (12) | 2.75g SMS | 5g Glycerol | 1.2g SA in 7g of glycerol | 4.5 hrs. | |
| (13) | 1.75g SMS (.37g SiO$_2$, .38g Na$_2$O) | 2g Glycerol | 0.6g SA in 11g glycerol | > overnight 1 hr. | |
| (14) | 1.75g SMS (.37 SiO$_2$, .38g Na$_2$O) | 2g Glyercol | 0.7g SA in 11g glycerol | > overnight | 1 hr. |
| (15) | 1.75g SMS (.37g SiO$_2$, .38g Na$_2$O) | 2g Glycerol | 0.8g SA in 11g glycerol | > overnight | 1 hr. |
| (16) | 1.26 PQ "D" (.37g SiO$_2$, .185g Na$_2$O) | None | 0.29g SA in 11g glycerol | — Set only at 60° C. for | 1 hr. |
| (17) | 1.26 PQ "D" (.37g SiO$_2$, .185g Na$_2$O) | None | 0.34g SA in 11g glycerol | 3 hrs. + | |
| (18) | 1.26 PQ "D" (.37g SiO$_2$, .185g Na$_2$O) | None | 0.39g SA in 11g glycerol | 1½ hrs. + | |
| (19) | 1.29 PQ "N" (.37g SiO$_2$, .115g Na$_2$O) | None | 0.18g SA in 11g glycerol | Overnight | Partially 1 hr. |
| (20) | 1.29g PQ "N" (.37g SiO$_2$, .115g Na$_2$O) | None | 0.21g SA in 11g glycerol | Overnight | Partially 1 hr. |
| (21) | 1.29g PQ "N" (.37g SiO$_2$, .115g Na$_2$O) | None | 0.24g SA in 11g glycerol | Overnight | Partially 2+ hrs. |
| (22) | 1.75g SMS | 2g Glycerol | 0.8g SA in 11g glycerol | — | 30 min. |
| (23) | 1.26g PQ "D" | 5g Glycerol | 0.39g SA in 8g glycerol | 4½–5 hrs. | 15 min. |
| (24) | 1.29g PQ "N" | 5g Glycerol | 0.24g SA in 8g glycerol | 1½ hrs. | 15 min. |
| (25) | 3.5g SMS | 3g Glycerol | 1.68g SA in 10g glycerol | 2 min. | |
| (26) | 2.5g SMS | 3g Glycerol | 1.2g SA in 10G glycerol | 5 hrs. | 10 min. |
| (27) | 1.5g SMS | 3g Glycerol | 0.72g SA in 10g glycerol | Partial 24 hr. | 45–60 min. |
| (28) | 2.0g PQ "D" | 5g Glycerol | 0.62g SA in 8g glycerol | 10 min. | 5 min. |
| (29) | 1.26g PQ "D" | 5g Glycerol | 0.39g SA in 8g glycerol | viscous at 5 hr. | 15 min. |
| (30) | 0.5g PQ "D" | 5g Glycerol | 0.15g SA in 8g glycerol | >25 hrs. | Partially at 24 |

The difference in gelling times between compositions (1)–(4) and (5)–(8) is due to the fact that the SMS solutions of compositions (1)–(4) were first placed in the freezer for several hours before adding the AA and probably resulted in precipitating some of the SMS from the glycerol thereby slowing the reaction between SMS and AA. It should be understood that in compositions (16)–(21), (23), (24) and (28)–(30), since the silicates PQ "D" and "N" are liquids, the glycerol was used to dissolve the SA.

Where acetic anhydride was used, the solution was obtained by adding the silicate to the glycerol, heating to dissolve and cooling to room temperature, then adding the acetic anhydride. Where succinic anhydride was used, the silicate was added to glycerol and heated to dissolve, and the succinic anhydride was also added to glycerol and heated to dissolve. Then the two solutions were mixed at room temperature.

In addition to the fact that gelling could be accelerated by heating the solutions to about 60° C., gelling could also be accelerated instead of delayed by adding water to the solutions. It was also observed that the solutions of PQ "D" silicates gelled at a pH between 8.5 and 9.0, solutions of PQ "N" silicates gelled closer to a

EXAMPLE I

| | | Wt. | % (W/W) |
|---|---|---|---|
| Sodium metasilicate .9H$_2$O (SMS) | = | 2.5g | 8.96 |
| Glycerol | = | 13.0 | 46.59 |
| Succinic anhydride (SA) | = | 1.2 | 4.30 |
| Pumice, medium (40.14%) | = | 11.2 | 40.14 |

The silicate is dissolved in 3 g glycerol with heating and the succinic anhydride is dissolved in 10 g glycerol with heating. When the solutions are cooled to room temperature, they are mixed and then the pumice is added with agitation to obtain a substantially homogeneous mass.

EXAMPLE II

Same as Example I except 13.9 g of pumice, medium (45.07%) is used, thus providing:

|  |  | % (W/W) |
|---|---|---|
| SMS | = | 8.22 |
| Glycerol | = | 42.76 |
| SA | = | 3.95 |
| Pumice | = | 45.07 |

EXAMPLE III

|  |  | Wt. | % (W/W) |
|---|---|---|---|
| Sodium metasilicate .9H$_2$O | = | 2.1g | 7.74 |
| Glycerol | = | 13.0 | 47.94 |
| Succinic anhydride | = | 1.02 | 3.76 |
| Pumice, medium (40.56%) | = | 11.0 | 40.56 |

The paste is prepared as in Example I.

EXAMPLE IV

Same as Example III except that 13.2 g of pumice, medium (45.02%) is used, thus providing:

|  |  | % (W/W) |
|---|---|---|
| SMS | = | 7.16 |
| Glycerol | = | 44.35 |
| SA | = | 3.48 |
| Pumice | = | 45.02 |

EXAMPLE V

|  |  | Wt. | % (W/W) |
|---|---|---|---|
| Sodium metasilicate .9H$_2$O | = | 1.7g | 6.72 |
| Glycerol | = | 13.0 | 49.90 |
| Succinic anhydride | = | 1.02 | 3.07 |
| Pumice, medium (40.3%) | = | 10.5 | 40.30 |

The paste is prepared as in Example I.

EXAMPLE VI

Same as Example V except that 12.7 g pumice, medium (44.95%) is used, thus providing:

|  |  | % (W/W) |
|---|---|---|
| SMS | = | 6.19 |
| Glycerol | = | 46.02 |
| SA | = | 2.83 |
| Pumice | = | 44.95 |

EXAMPLE VII

Same as Example V except that 15.5 g pumice, medium (49.92%) is used, thus providing:

|  |  | % (W/W) |
|---|---|---|
| SMS | = | 5.64 |
| Glycerol | = | 41.87 |
| SA | = | 2.58 |
| Pumice | = | 49.92 |

EXAMPLES VIII-X

|  | VIII | IX | X |
|---|---|---|---|
| Pumice, medium | 40.00g | 42.00g | 44.00g |
| Glycerol | 50.32 | 48.32 | 46.32 |
| SMS | 6.50 | 6.50 | 6.50 |
| SA | 3.12 | 3.12 | 3.12 |
| Color (green) | 0.02 | 0.02 | 0.02 |
| Saccharine | 0.03 | 0.03 | 0.03 |
| Methyl salicylate | 0.04 | 0.04 | 0.04 |

The SA is dissolved in 35 ml glycerol and color added. The SMS is dissolved in the remainder of the glycerol. The SA and SMS glycerol solutions are mixed at room temperature and the saccharine added, then the pumice and methyl salicylate are added and mixed to produce a substantially uniform mass which is poured into capsule containers under very low pressure prior to gelling to provide unit doses.

EXAMPLES XI-XIII

|  | XI | XII | XIII |
|---|---|---|---|
| SMS | 3.25g | 3.25g | 3.25g |
| Glycerol | 22.75 | 22.00 | 21.50 |
| SA | 1.56 | 1.56 | 1.56 |
| Flour | .75 | 1.50 | 2.25 |
| Pumice, medium | 21.70 | 21.70 | 21.70 |

The paste is prepared as in Examples VIII-X.

EXAMPLES XIV-XV

|  | XIV | XV |
|---|---|---|
| SMS | 2.50g | 1.50g |
| Glycerol | 22.00 | 22.00 |
| SA | 1.20 | 0.72 |
| Flour | 2.25 | 2.25 |
| Pumice, medium | 22.00 | 22.00 |

The paste is prepared as in Examples VIII-X.

The optimum range of ingredients in pastes employing sodium metasilicate, succinic anhydride and pumice was found to be about 6–6.5% sodium metasilicate, about 2.9–3.1% succinic anhydride and about 42–44% pumice, all by weight.

What is claimed is:

1. A substantially non-aqueous dental prophylactic paste comprising about 40–60% by weight of an abrasive, a humectant, a soluble alkaline silicate and an acid-forming agent selected from the group consisting of anhydrides, amides and esters, the silicate being present in an amount of about 5–10% by weight and the acid forming agent in an amount of about 2–5% by weight.

2. The dental prophylactic paste of claim 1 wherein the soluble alkaline silicate is selected from the group consisting of alkali metal silicates and quaternary ammonium silicate.

3. The dental prophylactic paste of claim 1 wherein the acid-forming agent is an anhydride.

4. The dental prophylactic paste of claim 3 wherein the anhydride is a four-carbon compound.

5. The dental prophylactic paste of claim 1 wherein the humectant is a glycol.

6. The dental prophylactic paste of claim 1 wherein the abrasive is pumice.

7. A substantially non-aqueous dental prophylactic paste comprising about 40–60% by weight of an abrasive, a humectant, an alkali metal silicate and an anhydride, the silicate being present in an amount of about 5–10% by weight and the anhydride in an amount of about 2–5% by weight.

8. The dental prophylactic paste of claim 7 in which the alkali metal silicate is selected from the group consisting of sodium metasilicate and sodium silicate and the anhydride is selected from the group consisting of succinic anhydride and acetic anhydride.

9. The dental prophylactic paste of claim 8 wherein the silicate is sodium metasilicate and the anhydride is succinic anhydride.

10. The dental prophylactic paste of claim 9 wherein the abrasive is pumice.

11. The dental prophylactic paste of claim 10 wherein the sodium metasilicate is present in an amount of about 6–6.5%, the succinic anhydride is present in an amount of about 2.9–3.1% and the pumice is present in an amount of about 42–44%.

* * * * *